US008336113B2

(12) United States Patent
Uttrachi

(10) Patent No.: US 8,336,113 B2
(45) Date of Patent: Dec. 25, 2012

(54) COOL, CLEAN AIR WELDING HELMET

(76) Inventor: Gerald Daniel Uttrachi, Florence, SC (US)

(*) Notice: Subject to any disclaimer, the term of this patent is extended or adjusted under 35 U.S.C. 154(b) by 467 days.

(21) Appl. No.: 12/661,066

(22) Filed: Mar. 10, 2010

(65) Prior Publication Data

US 2011/0219506 A1   Sep. 15, 2011

(51) Int. Cl.
*A61F 9/06* (2006.01)
*A61F 9/00* (2006.01)
*A42C 5/04* (2006.01)

(52) U.S. Cl. ........................... 2/8.6; 2/7; 2/171.3
(58) Field of Classification Search ............ 2/7, 8.1–8.8, 2/171.3, 209.13, 905, 906, 422, 435, 436, 2/437; 128/201.22, 201.25, 863
See application file for complete search history.

(56) References Cited

U.S. PATENT DOCUMENTS

| | | | | |
|---|---|---|---|---|
| 3,413,972 A | * | 12/1968 | Depping | 128/201.23 |
| 3,535,707 A | | 10/1970 | Greenlee | |
| 3,548,415 A | | 12/1970 | Walters | |
| 3,736,927 A | * | 6/1973 | Misaqi | 128/201.25 |
| 4,172,294 A | * | 10/1979 | Harris | 2/171.3 |
| 4,293,757 A | * | 10/1981 | Niemi | 219/147 |
| 4,463,569 A | * | 8/1984 | McLarty | 62/3.2 |
| 4,483,021 A | * | 11/1984 | McCall | 2/7 |
| 4,551,857 A | * | 11/1985 | Galvin | 2/7 |
| 5,040,381 A | * | 8/1991 | Hazen | 62/3.2 |
| 5,193,347 A | | 3/1993 | Apisdorf | |
| 5,655,374 A | * | 8/1997 | Santilli et al. | 62/3.5 |
| 5,896,579 A | | 4/1999 | Johnson | |
| RE36,242 E | | 6/1999 | Apisdorf | |
| 6,430,935 B1 | * | 8/2002 | Klett et al. | 62/3.3 |
| 6,954,944 B2 | * | 10/2005 | Feher | 2/171.3 |
| 7,178,932 B1 | | 2/2007 | Buckman | |
| 7,296,304 B2 | * | 11/2007 | Goldsborough | 2/171.3 |
| 7,534,005 B1 | | 5/2009 | Buckman | |
| 7,827,620 B2 | * | 11/2010 | Feher | 2/171.3 |
| 7,926,118 B2 | * | 4/2011 | Becker et al. | 2/8.2 |
| 8,087,254 B2 | * | 1/2012 | Arnold | 62/3.5 |
| 8,156,570 B1 | * | 4/2012 | Hockaday | 2/7 |

(Continued)

OTHER PUBLICATIONS

Chino Hayashi and Hiromi Tokura; "Effects of Head Cooling on Sweat Rate in Exercising Subjects Wearing Protective Clothing and Mask for Pesticide"; Applied Human Science Journal of Physiological Anthopology vol. 15 (1996), No. 4 pp. 149-154 See Abstract which provides a good summary showing sweat on arms reduced with head cooling etc.

(Continued)

*Primary Examiner* — Shelley Self
*Assistant Examiner* — Jane Yoon

(57) ABSTRACT

An improved welding helmet encloses a welders head and a portion of the neck. The helmet contains a fan, filter and thermoelectric cooling module to provide clean, cool air that reduces welding fume levels below suggested maximums and provides cool air to the welders head and neck area making their body feel cooler. Air exhausted from the helmet is captured and further utilized to significantly improve system efficiency by causing it to be in contact with the hot side heat sink that is a part of the thermoelectric cooling module assembly. The use of an external power source, including readily available welding power, is suggested as one option for supplying system power. An optional configuration is presented where an external container strapped to the welders body is employed containing the fan, air filter and thermoelectric cooling module and is connected to the helmet by cool air intake and exhaust air hoses.

10 Claims, 10 Drawing Sheets

U.S. PATENT DOCUMENTS

| | | | |
|---|---|---|---|
| 8,201,273 B2 * | 6/2012 | Duncan | 2/202 |
| 2006/0053529 A1 * | 3/2006 | Feher | 2/171.3 |
| 2007/0056073 A1 | 3/2007 | Martin | |
| 2008/0073330 A1 * | 3/2008 | Diedrick et al. | 219/133 |
| 2009/0055987 A1 * | 3/2009 | Becker et al. | 2/8.6 |
| 2009/0210988 A1 * | 8/2009 | Becker et al. | 2/8.6 |
| 2009/0210989 A1 * | 8/2009 | Becker et al. | 2/8.6 |
| 2010/0005572 A1 * | 1/2010 | Chaplin | 2/411 |

OTHER PUBLICATIONS

U.S. Appl. No. 12/455,067, filed May 29, 2009, Gerald D. Uttrachi.

* cited by examiner

COOL, CLEAN AIR WELDING HELMET

BACKGROUND

1. Field of Invention

This welding helmet invention improves welder comfort using a thermoelectric device and a quality filter to deliver clean, cool air to a welders head and neck. It utilizes an innovative design to more than double the energy efficiency required to achieve the very positive result.

2. Background

Welding is considered a hot and dirty occupation by many professional welders. Recently, allowable maximum levels of fume constituents from arc welding are at such low levels that conventional means of staying below these levels are not sufficient. For example, the current maximum recommended fume exposure level for some chrome (VI) compounds is 0.01 mg/m$^3$. Even employing source capture may not be sufficient to assure welder exposure levels are below that maximum safe level. When welding steel, some fume constituents may also exceed newly reduced maximum fume constituent levels. This may require a welder to use a high quality respirator under their normal welding helmet making the hot working environment even more objectionable. Welding often occurs in shops which are not cooled in warm weather and the use of devices such as respirators makes the welding occupation less attractive. When welding in very toxic environments air has been delivered to welding helmets from an external source through a long hose. This is not practical or desirable for most welding applications.

3. Description of Prior Art

There have been welding helmet designs that attempt to address some of the environmental problems encountered while welding:

(a) Walters in U.S. Pat. No. 3,548,415 (1968) entitled "Air Conditioned Helmet," describes a device that incorporates a fan enclosed in an open helmet, not one used for welding. It discusses several means of creating cooling such as gels, heat pipes and mentions but does not elaborate on the possible use of a thermoelectric principle. As with many of the devices reviewed, this one relies on battery power. It also does not mention any means of reducing welding fume levels to a very low level nor would the design with its open helmet arrangement accomplish this task.

(b) Greenlee in U.S. Pat. No. 3,535,707 (1970) entitled "Welding Helmet and the Like," describes a welding helmet with a fan in the front which draws air from the rear of the helmet. The back of this helmet, as with most welding helmets, is open. At the very low allowable concentrations of some welding fume constituents this approach would not provide sufficiently low fume breathing air in many welding applications.

(c) Martin, et al in a US patent application 2007/0056073 entitled "Modular Auto-Darkening Welding Filter," discusses a feature that would be used in this invention, an adjustable shade auto-darkening welding lens using external knobs to adjust some of the functions of the helmet. External adjustment of auto-darkening welding lens shade is common to some commercial welding helmets.

(d) Apisdorf in U.S. Pat. No. 5,193,317 (1993) and reissue Pat. RE 36,242 (1999) entitled "Helmet-Mounted Air System for Personal Comfort," describes the use of a helmet that incorporates a thermoelectric device to cool the air brought in by a fan. The helmet is open such that the cool air exits the helmet after passing the welders face one time and the cool air does not assist cooling the thermoelectric hot side heat sink. The patent claims the use of a battery that is body mountable to power the device. They discuss the small amount of cooling the device provides and justify the low amount as being sufficient to cause comfort. They emphasize the cool air is brought to the face and the design shows it exits the helmet area after it enters. They appear to justify low levels of flow and a small amount of cooling to support a key claim for the device of being capable of using a body mountable battery.

(e) Buckman in U.S. Pat. No. 7,534,005 (2009) entitled "Welding Helmet," and prior U.S. Pat. No. 7,178,932 describes the use of multiple fans and a filter. One figure also shows a type of helmet skirt. However, the claims describe a conventional welding helmet with only front and sides, not the back or the top of the welders head covered. There is also no mention of a cooling device of the thermoelectric type or of any type that would significantly improve the welder's temperature environment.

(f) Johnson in U.S. Pat. No. 5,896,579 describes a welding helmet with a fan and a device for employing evaporation cooling. As with most of the prior art discovered the helmet described also has a typical open back and would not provide the sufficiently clean breathing air needed in many welding environments.

(g) Goldsborough in U.S. Pat. No. 7,296,304 describes a race car crash helmet that contains Peltier thermoelectric modules located around the periphery of the helmet shell. However the cooled air exits the helmet at the bottom and other openings and is not sealed. This patent does discuss providing power from a cigarette lighter receptacle which is readily available in a conventional automobile. However there is no attempt to filter the air or improve efficiency by using the cooled air exhausted from the helmet to assist in cooling the thermoelectric hot side heat sinks.

SUMMARY, OBJECTS AND ADVANTAGES

It is the object of this present invention to provide cool, clean air to a welder by incorporating a number of unique elements and features in a helmet design for the welding profession. Studies have shown that head cooling reduces sweating in other parts of the body. These features provide an improved environment for the welder and cause welders to desire to use the device because of the improved working conditions. The device further utilizes clean, cooled air exiting the helmet to improve the energy efficiency of the thermoelectric cooling module by causing the helmet exhaust air to flow through the thermoelectric module hot side heat sink. In tests of this hot heat sink cooling approach a surprising result was found. Over twice the amount of temperature reduction was achieved by utilizing the helmet exhaust air to help cool the hot side heat sink compared to when it was not employed.

This welding helmet is also unique compared to what is used in industry and that defined in prior art. One unique feature is the functional shape of the welding helmet. One embodiment has an external shape like an automotive racing helmet or a full face motorcycle helmet. That is, not only is it enclosed on the front and sides but also on the top and back. It utilizes a skirt made from a flexible material attached to the bottom of the helmet opening. The skirt can be placed snuggly around the neck with an appropriate tie device and or tucked into a shirt or welding jacket to assist in capturing the cooled helmet exhaust air. The skirt will also reduce the intrusion of outside air which may have excessive levels of potentially harmful fumes. Unlike a racing or motorcycle helmet the current invention can be made from light weight materials only having to meet penetration tests to be certified by the American National Standards Institute. If desired it could be constructed to also meet the requirements for a hard hat where needed in construction, shipyards and in many manufacturing plants.

By employing an enclosed helmet it is possible to use a fan to assure breathing air passes through a quality replaceable filter designed to capture potentially harmful welding fume particles. Two versions of the helmet device are defined. In one version, the filter is placed at the back of the helmet where it is exposed to the least amount of welding fume. Air entering the helmet is channeled through an internal passageway near the top of the helmet above a head band. The head band provides for a custom fit for the wearer. A thermoelectric cooling module powered by a DC electric current causes one surface to become cooler than ambient and the other to become hotter. The thermoelectric module utilizes finned or a pin type heat sink on both cool and hot sides. The cold side heat sink is placed in an air passageway with the filter on one end. An internal fan causes filtered air to come in contact with the cold heat sink before routing past the welders face and head. The thermoelectric modules hot heat sink heat transfer surface is placed outside the surface of the helmet and dissipates heat to the outside air. To significantly assist in removing heat from the hot side heat sink, the air exhausted from the helmet having accomplished the task of cooling the welders face can be channeled to the hot side heat sink. A cowl arrangement is employed to focus the cooled clean air to maximize contact with the heat sink. The electric powered fan has sufficient power to provide the needed air flow to meet the welders breathing health and safety requirements. Optionally an additional fan can be placed on or near the hot side heat sink to assist overall air movement and to enhance heat removal. It was discovered by using the cool helmet exhaust air to help cool the thermoelectric modules hot side heat sink over twice the reduction in air temperature was be achieved. In addition, this cooled, clean air helps reduce the hot heat sinks exposure to welding fumes and metal grinding dust. Keeping the heat sink clean is important to maintaining system performance.

The welding lens employed should be of an auto-darkening type. When an arc is struck it switches from essentially a clear lens to one darkened sufficiently to protect the welder's eyes from the arc rays. It allows good vision when not welding and provides adequate blockage of arc rays when welding. It is possible to hinge the portion of the helmet containing the auto-darkening lens mechanism so it can be raised allowing the welder an opening directly to the outside. This requires a quality sealing system to avoid welding fumes entering around the helmet section containing the lens. It is also possible to have a clear material covering the opening when the hinged portion of the helmet with the auto-darkening lens is raised. This would protect the welder so they might be able to grind or perform fitting tasks while maintaining the cool environment. Since a number of viable mechanisms are available that would facilitate this possible embodiment, it is assumed one skilled in the art could implement this feature if desired and details are not covered in the patent claims.

The second version of the helmet device is one where the thermoelectric module, heat sinks, filter and fan(s) are located in a separate canister that the welder can carry using shoulder straps, a belt or backpack. Cool, clean air is created in the canister and flows through a hose to the top-front of the welding helmet where it cools the welder. Helmet exhaust air is transported through an exhaust hose to a section of the canister past the hot side thermoelectric module heat sink also located in that section. This approach provides for the use of a lighter helmet.

Supplying power for the helmet or external canister version for a desired length of time may be difficult to achieve with a reasonable weight of batteries. Other energy storage devices which have more energy storage per a given weight than a battery may be viable such as fuel cells or mechanical energy storage devices. In addition, several unique characteristics of welding provide an opportunity to power the clean, cool welding helmet with minimum connections and without long electrical lines, namely:

a) Arc welding requires a great deal of electrical energy. The major welding process used in industry is referred to as MIG welding (Metal Inert Gas) or the official designation in the US is Gas Metal Arc Welding (GMAW.) The term MIG welding will be used for this patent. MIG welding employs a continuously fed wire made of either steel, aluminum, stainless steel or other metal depending on the material being welded. For steel and stainless steel the wire can be solid or a product called cored wire where granular powder or flux ingredients are placed in the center of a tubular wire structure. Over 99% of these MIG welding processes utilize DC welding power ranging, for industrial systems, from 200 to 600 amperage capacity. Welding voltage typically ranges from 20 to 35 volts. It is possible to connect the helmet to this source to power with no ill effects on welding machine performance. Since welder safety is of paramount importance it is desirable to have the voltage going to the helmet to be less than about 24 volts. It is possible to reduce the welding voltage through appropriate circuitry and provide power at a safe voltage such as 12 to 18 volts. Since the MIG welding torch is typically about 3 meters in length, connecting the required DC power wire from the helmet to this low voltage DC source at the MIG wire feeder will require a minimum length power wire. With most MIG welders the DC voltage is not available when welding is stopped. It may be desirable to have the helmet powered between welds. Therefore, a battery could be incorporated in the DC converter device. Since MIG wire feeders are generally somewhat bulky and heavy, often including 20 kg or more of wire, the extra weight of a battery would normally not be a problem when placed at this location. The DC converter device could incorporate a system that charged the battery when welding. There would also be a ground connection needed to power the converter which could be connected to the work piece where the welding ground cable is attached.

b) Stick welding is another common arc welding process used in industry and provides and even easier method of powering the helmet. The formal designation for this process is Shielding Metal Arc Welding (SMAW.) Stick welding will be used to describe the process in this patent. In most instances, stick welding power supplies are energized with welding voltage whether an arc is struck or not. Therefore a converter to create the low voltage DC power can be relatively small and compact. Even if the stick welding power is AC it can easily be converted to low voltage DC required for powering the helmet. The helmet power wire could be connected between the stick power line coming from the power supply and the short length of power cable that is usually attached to the stick electrode holder which is held by the welder. The cable supplying power to the helmet could be less than 3 or 4 meters long. The welding operator would connect their helmet power wire to the DC converter located where the stick electrode holder is connected to the stick power line. There would also be a ground connection needed to power the converter which can be connected to the work piece where the welding ground cable is attached.

c) If desired, a power supply system could be used that is similar to that employed to power a laptop computer or other devices that operate at low DC voltage. As with computer power supplies it could be plugged into any available AC power source. Many welding power supplies incorporate auxiliary AC power receptacles to power devices such as grinders. These AC receptacles can be conveniently used to provide the required helmet power.

d) A fourth alternative to power the self contained helmet for a limited time could be the use of a backpack to carry a rechargeable battery or a fuel cell or an electromechanical energy storage device or other suitable energy storage device. These portable power device options could be attached directly to the canister version of the cool, clean helmet system.

There are several advantages of the proposed device over alternatives. To meet the increasingly lower maximum fume exposure levels, the use of quality respirators may be the only alternative choice for a number of applications. Respirators, even when used correctly, require a doctor to define if a worker is capable of breathing through these devices for an 8 hour day. Breathing through a respirator creates more stress on the heart. Some welders elect to have beards or mustaches. Facial hair is usually not allowed to properly fit a quality respirator. The heat involved when welding is often a complaint of welders. The potential to have a cooler work environment will offset the somewhat more confining helmet. The use of this helmet is a better alternative than using a conventional welding helmet and wearing a respirator.

Several additional benefits occur when having a fully enclosed welding helmet. The hot sparks from welding, called spatter, are prevented from hitting the top and back of the head causing burns. This is particularly an issue with current welding helmets when welding overhead or when other welders are in the immediate area. The proposed helmet also employs a skirt material that protects the neck area from spatter hitting the skin eliminating burns.

DRAWING FIGURES

DESCRIPTION

Main Embodiment

Figure 1:
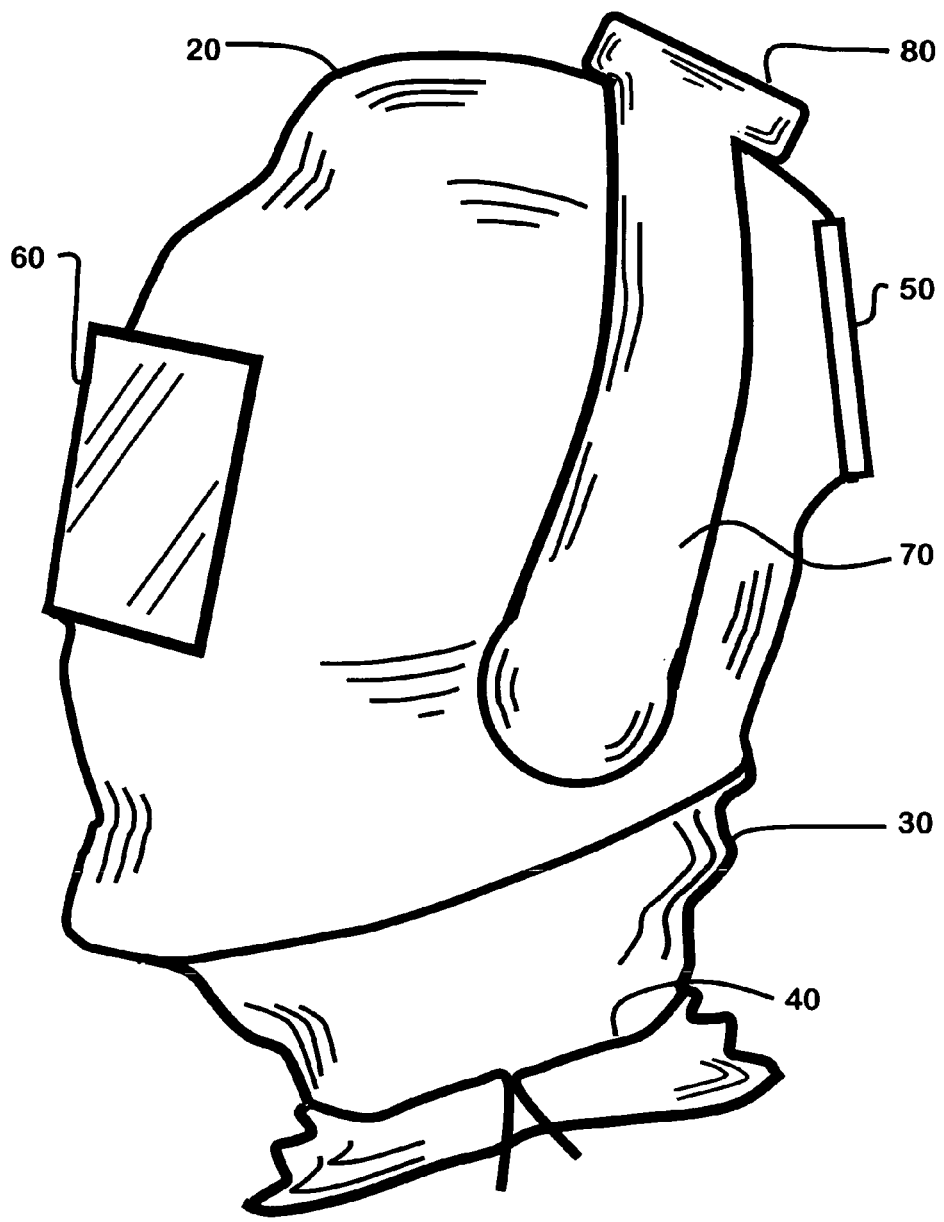
FIG. 1 is a left side view of the helmet, skirt, skirt tie, filter, exhaust air passage and cowling.

FIG. 1 illustrates a welding helmet 20 as viewed from the left side. The visible elements include helmet 20 that encloses the welding operators head in the front, right side, left side, top and back. A raised area at the top of helmet 20 contains an internal air passageway 125 FIG. 3 that exists between a helmet baffle 120 FIG. 3 and the top inner surface of helmet 20. Helmet air filter 50 is located at the rear of helmet 20 and the inlet end of the internal air passageway 125 FIG. 3. The hot heat sink cowling 80 surrounds the helmet hot heat sink 90 FIG. 3 on all but one open side and is in intimate contact with a thermoelectric module 330 FIG. 8 that is not viable but is sandwiched between the helmet hot heat sink 90 FIG. 3 and helmet cold heat sink 150 FIG. 3, both of which are partially visible in FIG. 3. A portion of the auto-darkening welding lens 60 is shown. Also visible is a skirt 30 that is attached to the bottom opening of the helmet 20 and minimizes external welding fumes from entering the helmet 20 and also assists in having a majority of the clean cooled air exiting helmet 20 passing through helmet exhaust air passage 70 and hot heat sink cowling 80. A tie 40 can be used to secure skirt 30 to the welding operator's neck. Skirt 30 can be of sufficient length to tuck under the welding operators shirt or welding jacket.

Figure 2:
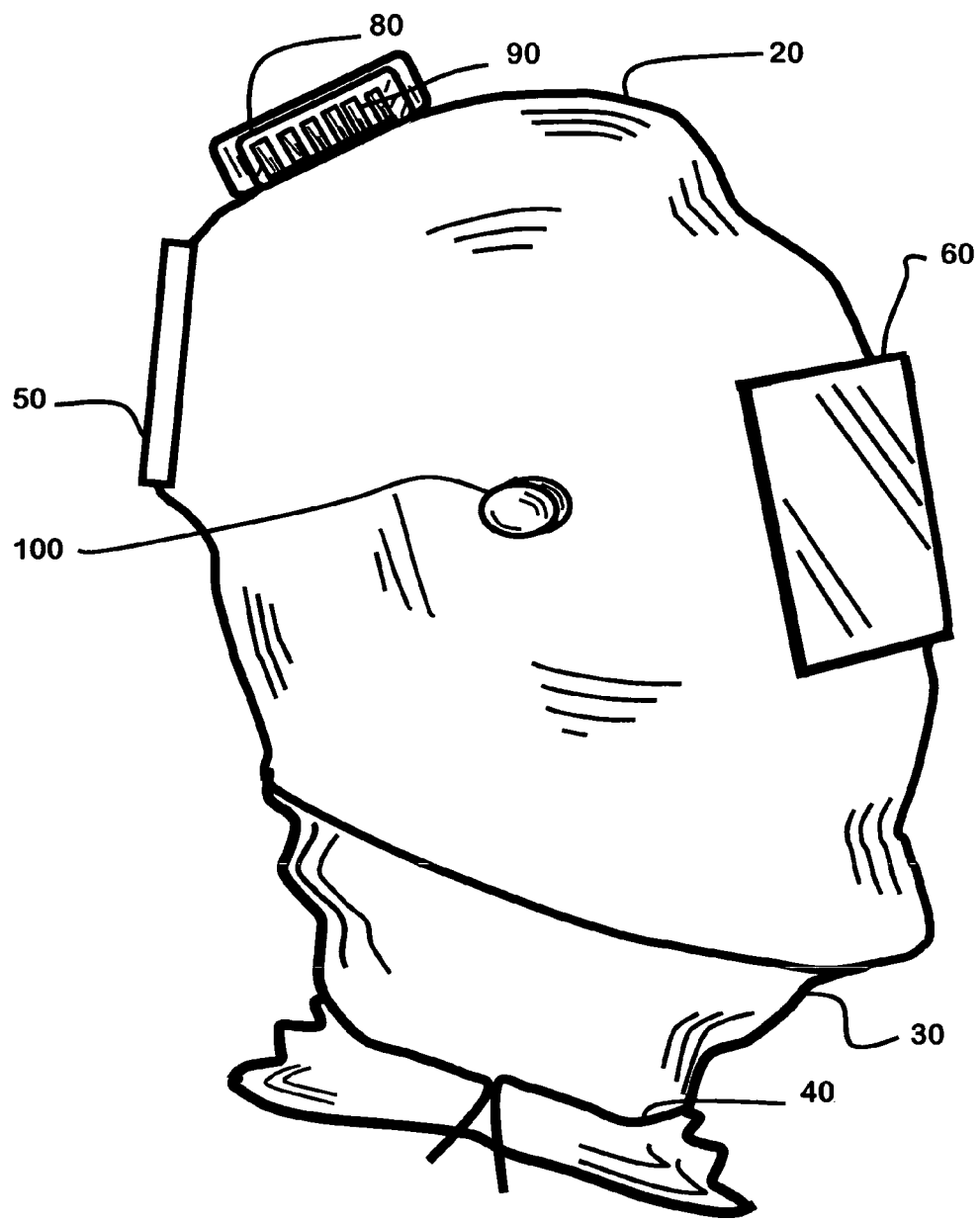
FIG. 2 is the right side view of the helmet, hot side heat sink and temperature control knob.

FIG. 2 illustrates helmet 20 as viewed from the right side. Helmet filter 50, welding lens 60, skirt 30 and tie 40 are visible. Hot heat sink 90 and the opening to the atmosphere of hot heat sink cowl 80 are shown. Helmet temperature control knob 100 is connected to helmet control module 160 FIG. 3.

Figure 3:
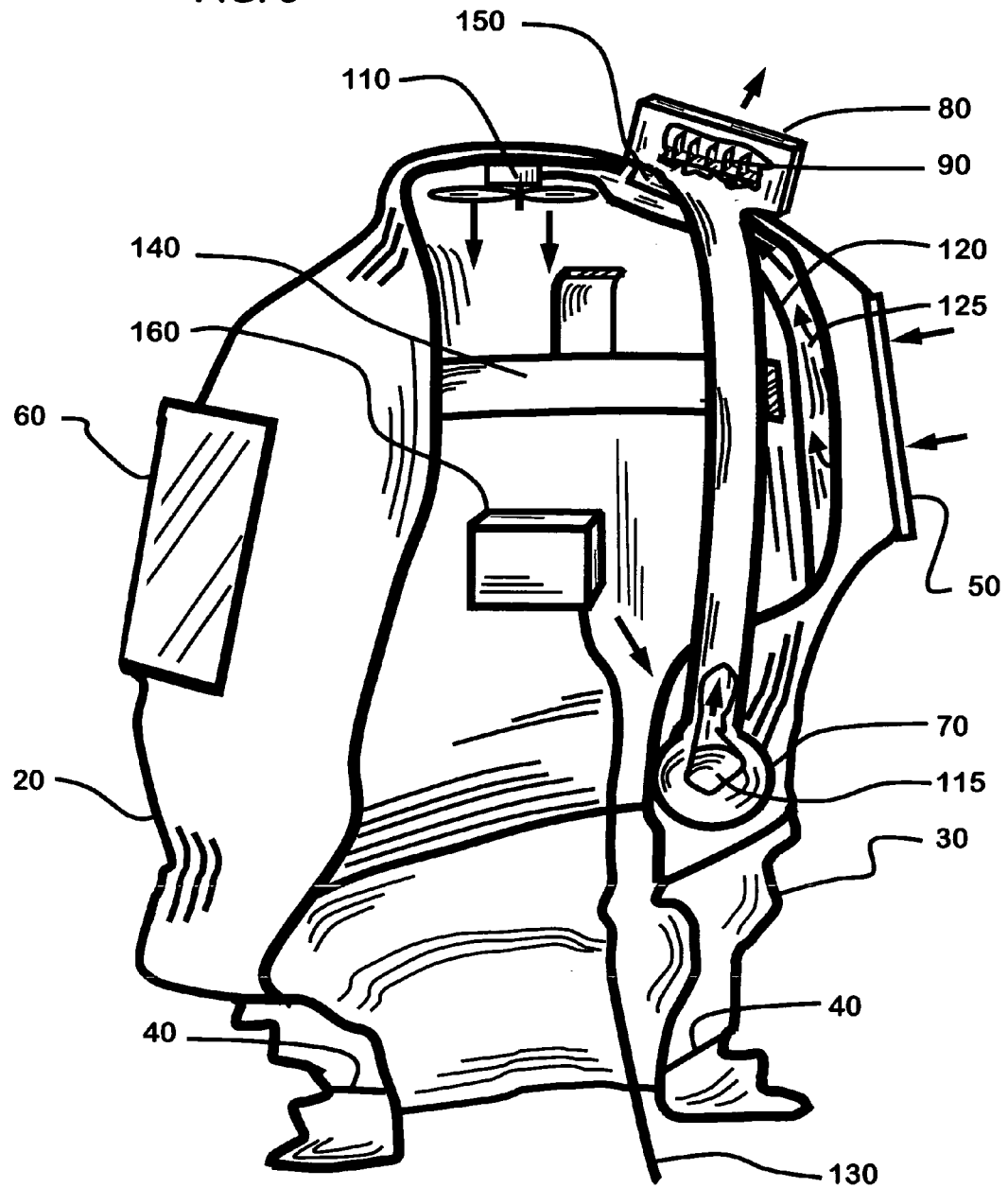
FIG. 3 is a left side helmet cutaway view showing baffle, air passageway, fan, head band, exhaust air passage, hot and cold heat sinks and control module.
Figure 8:
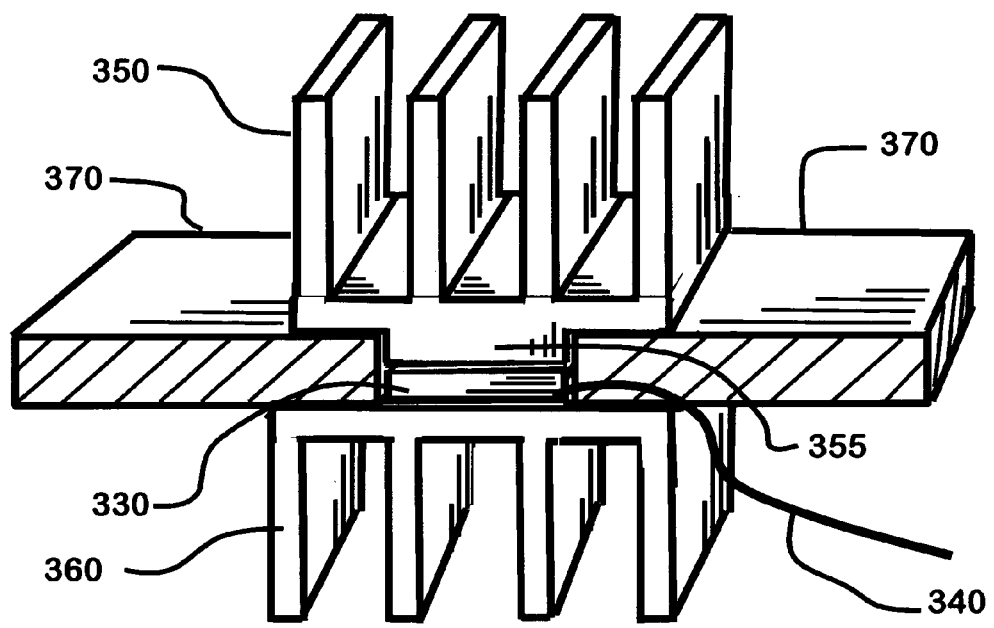
FIG. 8 is a thermoelectric module shown sandwiched between the hot and cold side heat sinks.

FIG. 3 shows a cutaway view of the left side of helmet 20 showing most of the key elements. Air flow is shown with arrows. The elements not previously shown include: helmet baffle 120 that directs air from helmet filter 50 through internal air passageway 125 past cold heat sink 150 to helmet cooling fan 110. Headband 140, helmet control module 160 and helmet vent opening 115 are also shown. The thermoelectric module 330 FIG. 8 is not shown since it is sandwiched between helmet cold heat sink 150 and helmet hot heat sink 90. A portion of helmet power wire 130 is also shown. The voltage proved by helmet power wire 130 should be limited to about 24 volts to enhance welder safety.

Figure 4:
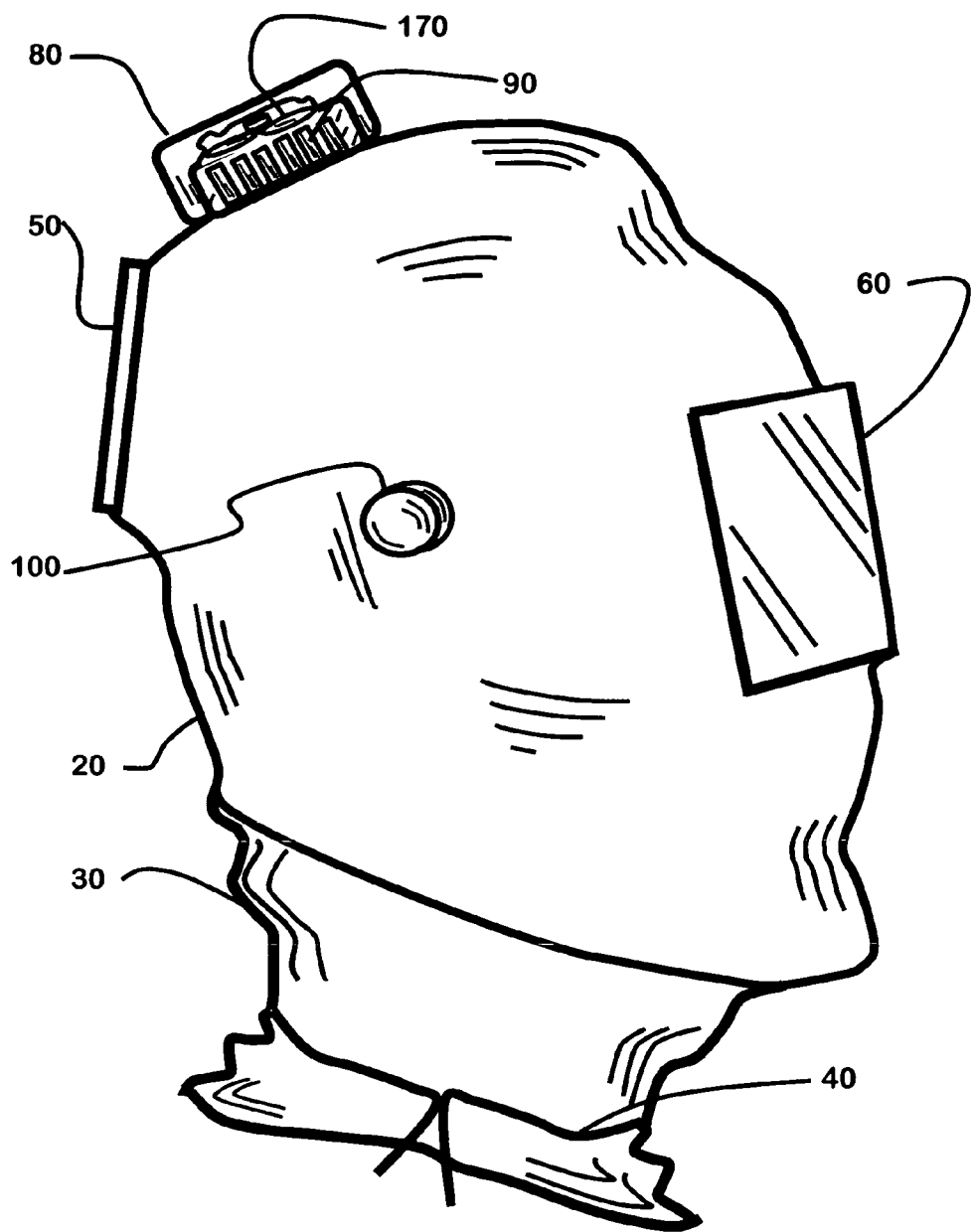
FIG. 4 is a left side helmet view with a cutaway of the cowling and hot side heat sink.

FIG. 4 is similar to FIG. 2 with the addition of an optional helmet hot heat sink fan 170 shown in a partial cutaway of hot heat sink cowling 80. Helmet 20, helmet filter 50, welding lens 60, skirt 30, tie 40 and helmet temperature control knob 100 are visible.

FIG. 8 shows a generic assembly of a thermoelectric module 330 sandwiched between hot heat sink 350 and cold heat sink 360. Thermoelectric module 330 is very thin and must be in intimate contact with hot heat sink 350 and cold heat sink 360. To be functional, baffle 370 must generally be thicker than thermoelectric module 330 so the hot heat sink 350 is shown having a thicker section 355 at the bottom to allow for the different thicknesses. The modular power wires 340 shown would be connected to either helmet control module 150 FIG. 3 or container control module 290 FIG. 5 or if neither is employed could be connected directly to thermoelectric module 330, helmet cooling fan 110 FIG. 3 or container cooling fan 220 FIG. 5. The cooling fins for hot heat sink 350 and cold heat sink 360 are shown parallel to each other as they would probably be as used with external container 180 FIG. 5 assembly however they can be at any angle if air flow is in different directions.

Figure 5:
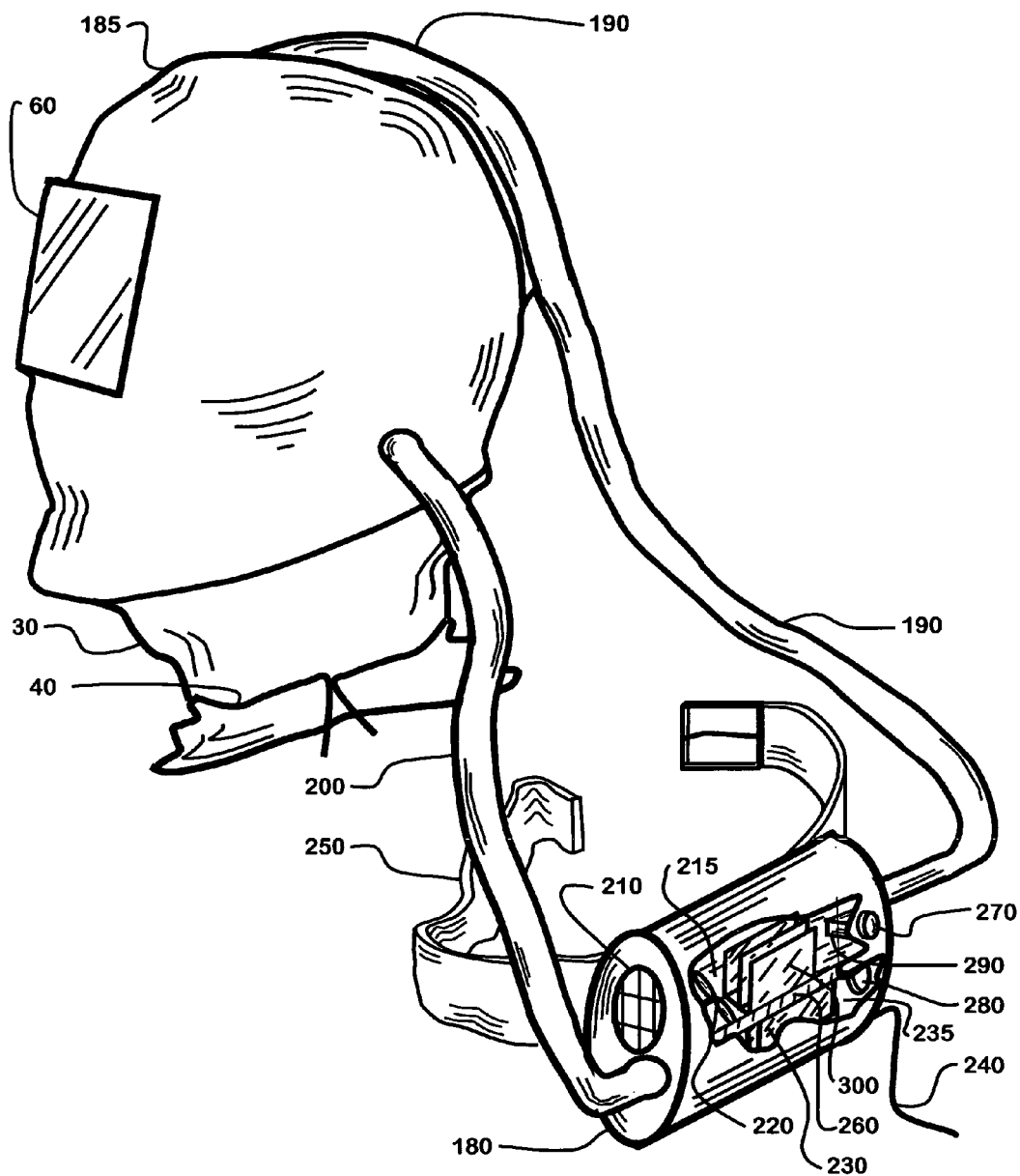
FIG. 5 is a view of the separate canister helmet system with external power.
Figure 9:
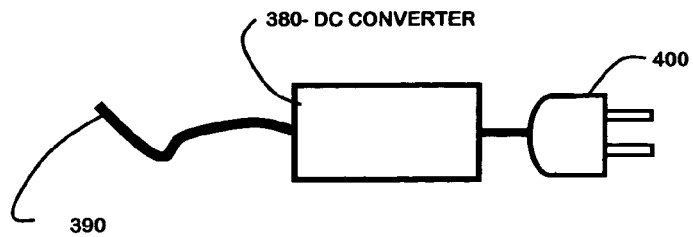
FIG. 9 is a DC converter connected to an AC power source to power the helmet.

FIG. 9 shows a way to power helmet 20 FIG. 1 or external container 180 FIG. 5 using an AC power source with a DC converter 380. The DC converter 380 produces low voltage DC power for welder safety. Power wire 390 can be connected directly to helmet 20 FIG. 1 or external container 180 FIG. 5. Plug 400 would fit into a normal AC electrical receptacle.

Figure 10:
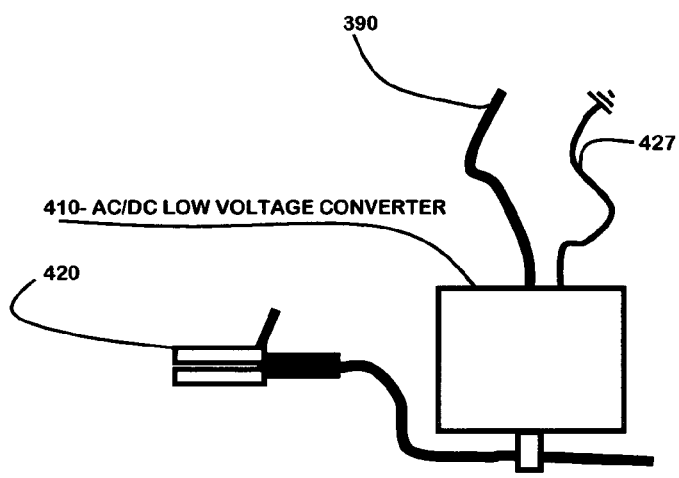
FIG. 10 is an AC/DC converter attached to stick welder power to power the helmet.

FIG. 10 shows a way to power helmet 20 FIG. 1 or external container 180 FIG. 5 by connecting to AC/DC Stick welding power using AC/DC low voltage converter 410. AC/DC low voltage converter 410 converts the higher voltage power from a Stick welding power to a safer low voltage DC. If the Stick welding power is AC the AC/DC low voltage converter 410 changes the AC power to low voltage DC. The AC/DC converter 410 connects between the Stick electrode holder 420 and the welding power line 425. The AC/DC low voltage converter 410 also has a ground wire connection 427 that can be attached where the welding power ground is connected.

Figure 11:
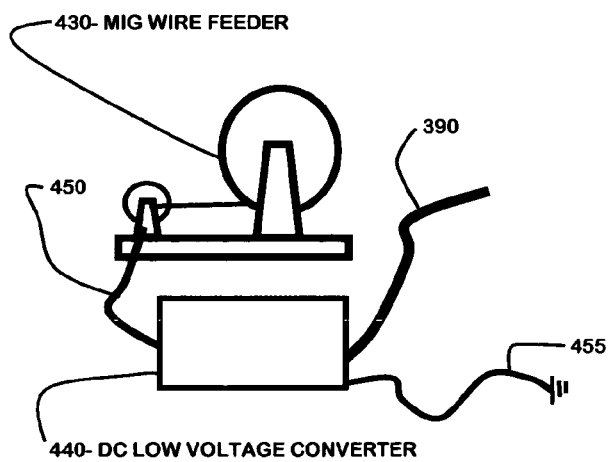
FIG. 11 is a DC converter attached to MIG welder power to power the helmet.

FIG. 11 shows a way to power helmet 20 FIG. 1 or external container 180 FIG. 5 by connecting to a MIG wire feeder power 430 using DC low voltage converter 440. DC low voltage converter 440 produces a safer low DC voltage. DC low voltage converter 440 can be connected directly at the MIG wire feeder 430 where welding power is available using feeder power wire 450. The DC low voltage converter 440 also has a MIG ground wire 455 that can be attached where the welding power ground is connected.

Figure 12:
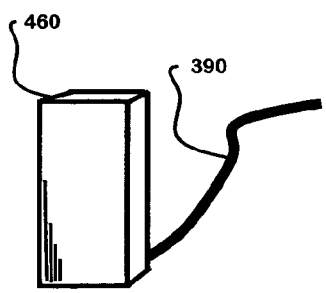
FIG. 12 is a portable power source that can be affixed to a welder with a strap arrangement.

FIG. 12 shows how helmet 20 FIG. 1 could be powered using an external energy storage device 460. The energy storage device 460 can be carried by the welder with appropriate means such as a strap, belt 250 or backpack. It could utilize rechargeable batteries, a fuel cell or similar device for providing electrical power. Power wire 390 connects directly to helmet 20 FIG. 1 or indirectly through an appropriate connector, such as energy source connector 480 FIG. 13.

Operation

Main Embodiment

Referring to FIG. 1. A welder places helmet 20 over their head having previously adjusted the head band 140 FIG. 3 for the proper fit. Skirt 30 is tucked under the welder's shirt and or the tie 40 is tightened so that the skirt 30 causes a majority of the air coming through helmet air filter 50 to be channeled through helmet vent opening 115 FIG. 3 through exhaust passage 70 to hot heat sink cowling 80 past helmet hot heat sink 90 FIG. 3. The welder than connects the helmet power wire 130 FIG. 3 to an appropriate power source such as defined in FIG. 9, FIG. 10, FIG. 11 or FIG. 12. Once power is supplied, the helmet cooling fan 110 FIG. 3 starts and pulls air though helmet air filter 50 through helmet vent opening 115 FIG. 3 into internal air passageway 125 FIG. 3. Power is also supplied to a thermoelectric module 330 FIG. 8 which is sandwiched between helmet hot heat sink 90 and helmet cold heat sink 150. The resulting stream of air in internal air passageway 125 FIG. 3 will contact the cool surface of helmet cold heat sink 150 reducing the air temperature. Helmet cold heat sink 150 and helmet hot heat sink 90 are constructed of a thermally conductive material and may contain cooling fins or pins to increase surface area. The welder immediately receives cool, clean air delivered over their head and face. The helmet air filter 50 would be replaced periodically as it becomes clogged with welding fumes, metal dust from grinding etc.

Referring to FIG. 2. In addition to the above operating description also shown is container temperature control knob 100. It is connected to a helmet control module 160 FIG. 3. The helmet temperature control knob 100 is used by the welding operator to adjust the air temperature to the desired level. The helmet control module 160 FIG. 3 uses a suitable means such as lowering voltage to adjust the amount of cooling achieved by the thermoelectric module 330 FIG. 8 that is sandwiched between the helmet hot heat sink 90 and the helmet cold heat sink 150 FIG. 3. A device could be incorporated in helmet control module 160 FIG. 3 to sense and adjust the temperature to a preset level automatically. The design of such devices is readily achievable by one skilled in the art and is not covered in this patent.

Description and Operation

Additional Embodiments

Referring to FIG. 5. An alternate configuration that provides a lighter helmet utilizes an external container 180 to house the required system elements, namely: container air filter 210, the container cold heat sink 300 transporting clean cool air through helmet inlet cooled air hose 190 to the hose supplied helmet 185. Skirt 30 is tucked under the welder's shirt and or tie 40 is tightened so that skirt 30 causes a majority of the air coming into hose supplied helmet 185 to be channeled through helmet exhaust air hose 200 back to external container 180. One construction configuration of external container 180 has an input air section 215 and an exhaust air section 235 separated by a container baffle 260. The external container 180, is attached to the welding operator by a suitable means, such as a belt 250 or shoulder straps.

In operation container power wire 240 is connected to a suitable power source such as defined in either FIG. 9, FIG. 10, FIG. 11 or FIG. 12. Power is supplied to a thermoelectric module 330 FIG. 8 that is sandwiched between container hot heat sink 230 and helmet cold heat sink 300. The container cold heat sink 300 and container hot heat sink 230 are constructed of a thermally conductive material and may contain cooling fins or pins to increase surface area. Air is pulled through container air filter 210 by container cooling fan 220 located in input air section 215. The air contacts container cool heat sink 300 also located in input air section 215. The clean cool air is transported through an opening, not shown, to a helmet inlet cooled air hose 190 and enters through an opening, not shown, in the top front of hose supplied helmet 185. The cool clean air then contacts the welders head and face. The clean cooled air then exits the hose supplied helmet 185 through an opening, not shown, into helmet exhaust air hose 200 and enters through an opening, not shown, in the exhaust air section 235 of external container 180. The air then contacts container hot heat sink 230 where it assists in removing heat. The air then exits external container 180 through exhaust air opening 280.

Referring to FIG. 5. In addition to the above operating description also shown are container temperature control knob 270 connected to a container control module 290. The container temperature control knob 270 is used by the welding operator to adjust the air temperature to the desired level. The container control module 290 uses a suitable means such as lowering voltage to adjust the amount of cooling achieved by the thermoelectric module 330 FIG. 8 that is sandwiched between the container hot heat sink 230 and the container cold heat sink 300. A device could be incorporated in container control module 290 to sense and automatically adjust temperature to a preset level. The design of such devices is readily achievable by one skilled in the art and is not covered in this patent.

If the option of using container temperature control knob 270 and container control module 290 is not employed, container cooling fan 220 could operate at one speed and a smaller capacity thermoelectric module 330 FIG. 8 utilized such that excess cooling cannot be achieved. It is also possible to use multiple lower power level thermoelectric module 330 FIG. 8 and selectively tuned each on or off with a simple switch to control temperature.

Figure 6:
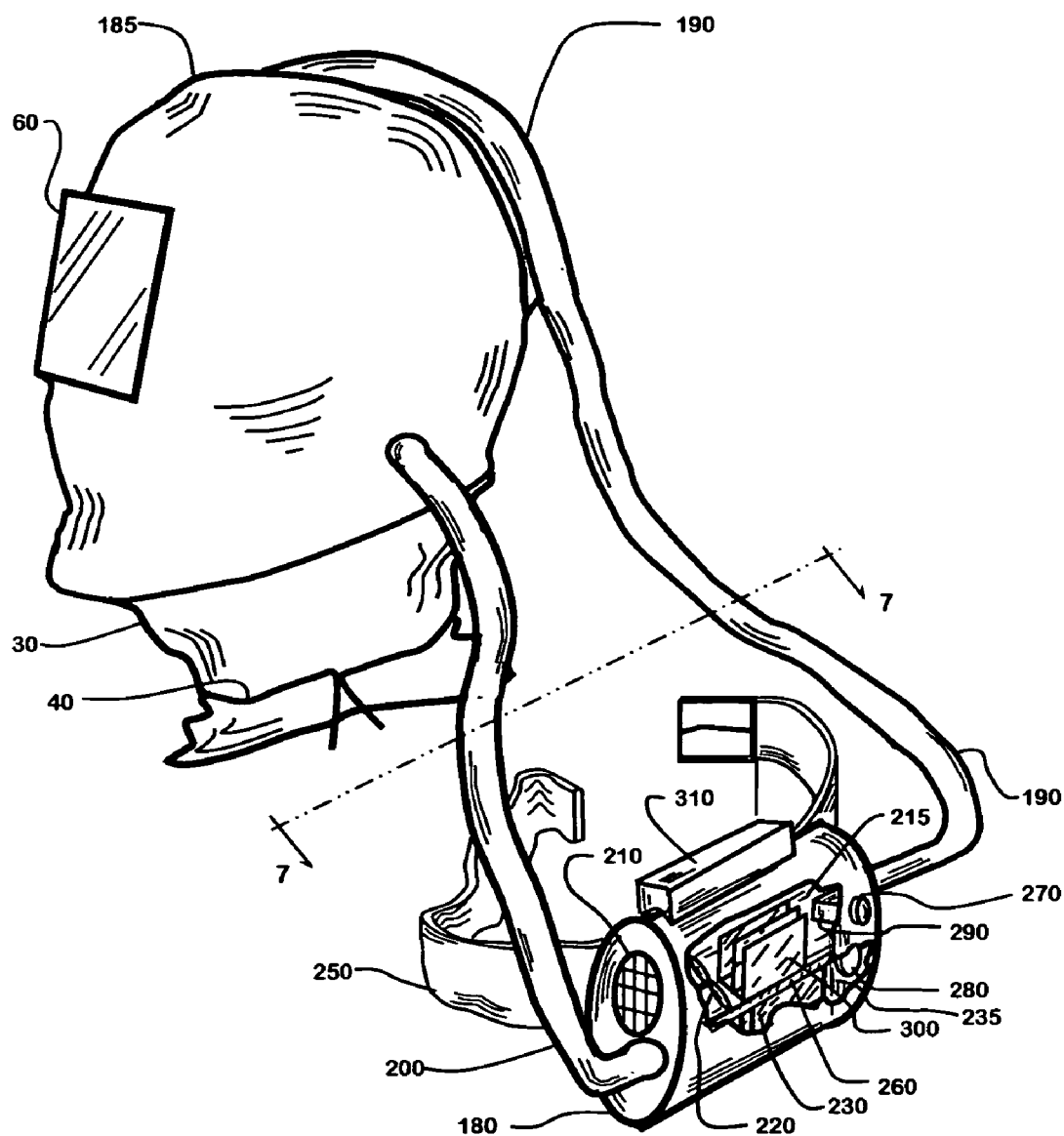
FIG. 6 is a view of the canister helmet system with a self contained energy source.

FIG. 6 shows the same elements as FIG. 5 with the elimination of the container power wire 240 and the addition of a stored energy device 310 that supplies the electrical energy needed to power the container cooling fan 220 and the thermoelectric module 330 FIG. 8 that is not shown in FIG. 6 since it is sandwiched between container hot heat sink 230 and container cold heat sink 300.

Figure 7:
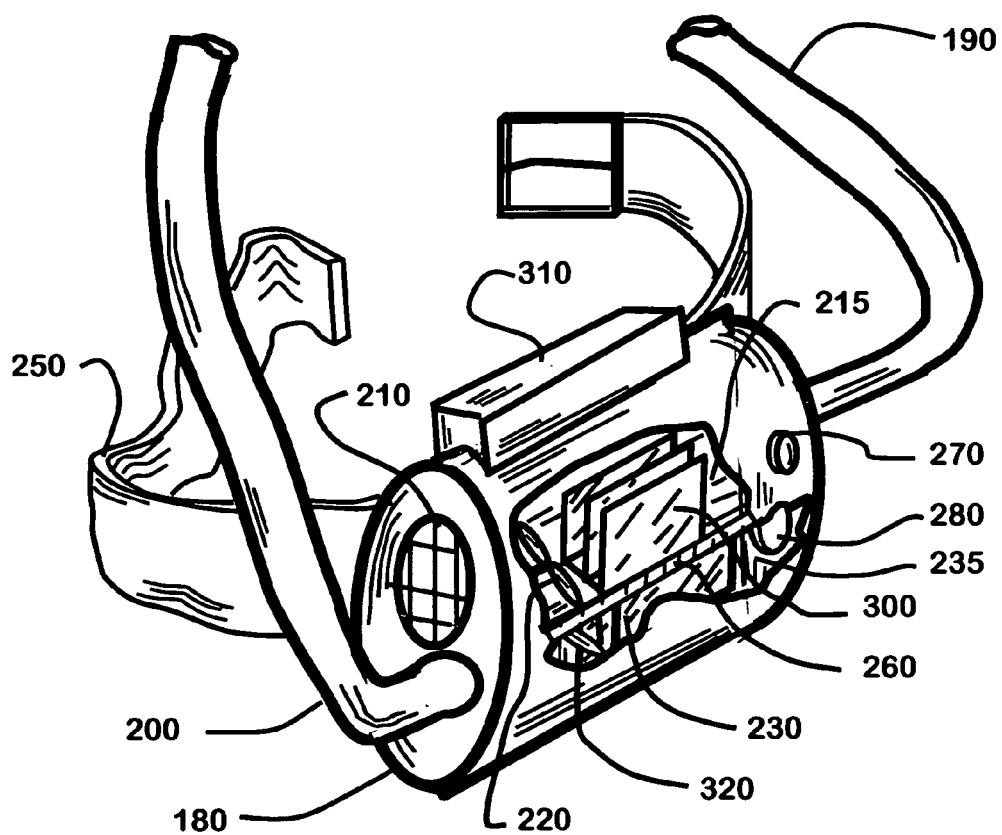
FIG. 7 is a large view of the canister portion of the helmet system shown in FIG. 6.

Referring to FIG. 7. The external container 180 exhaust air section may contain an optional container hot heat sink fan 320 to increase the total system air flow including the volume of air in contact with container hot heat sink 230. The helmet hot heat sink fan 320 can also assist in keeping fumes and dust particles from entering the external container exhaust air opening 280.

Figure 13:
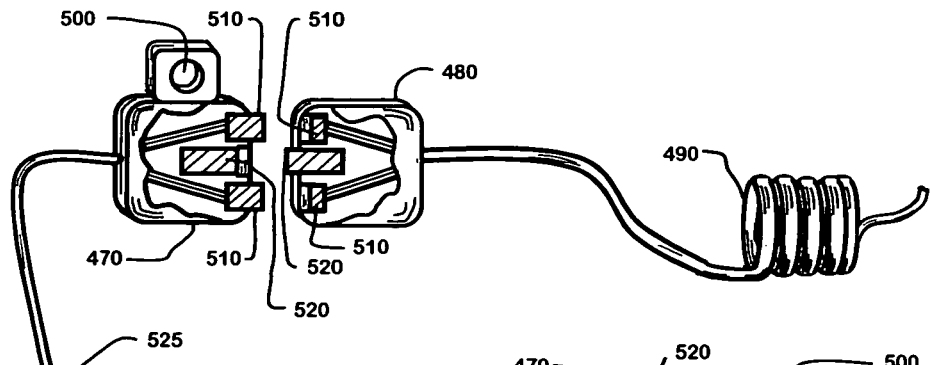
FIG. 13 is a possible quick connect device to help manage the helmet power tether.

FIG. 13 shows an optional device to avoid possible breaking problems if helmet power wire 130 FIG. 3 or container power wire 240 FIG. 5 were to be connected directly to power wire 390 FIG. 9. To use this device, connector power wire 525 would be connected to helmet power wire 130 FIG. 3 or container power wire 240 FIG. 5 and coiled power wire 490 would be connected to power wire 390 FIG. 9. A DC power connector 470 quickly attaches to an energy source connector 480 using magnets 520. Electrical contacts 510 in the DC power connector 470 protrude slightly and insert into recesses in energy source connector 480 to the electrical connectors 510 located in energy source connector 480. The magnets 520 are offset to assure the electrical contacts 510 meet before the magnet 520 touches the mating magnet 520. The coiled wire to power source 490 reduces the possibility of tangles. An attachment hole 500 is affixed to the DC power connector 480 so a welder can attach it to part of their apparel. There are a number of ways this function can be accomplished so it is not defined by the patent claims.

Figure 14:
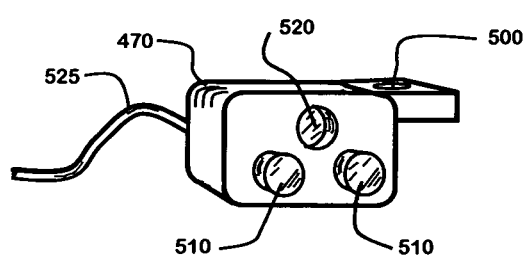
FIG. 14 is an end view of the quick connect device shown in FIG. 13.

FIG. 14 is another view of the DC power connector 470 showing the electrical contacts 510 protruding and the magnet 520 recessed. The attachment hole 500 is also shown.

Figure 15:
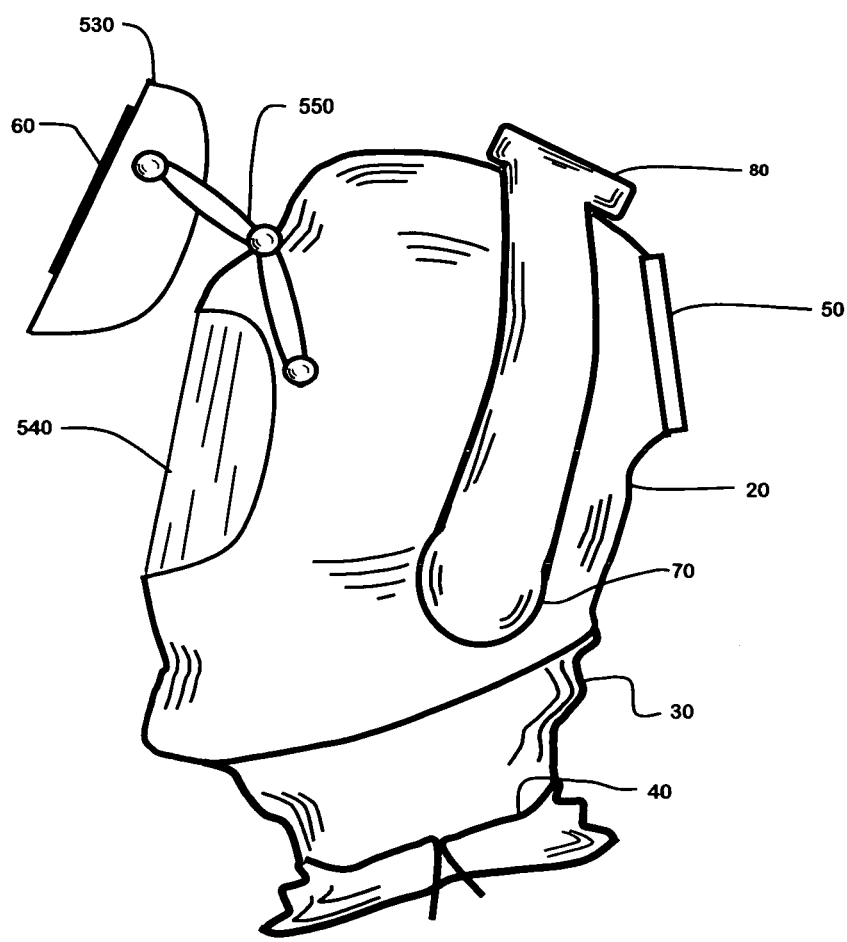
FIG. 15 shows the helmet with a possible swing away front section.

FIG. 15 is a view of the welding helmet showing a possible way a helmet segment with lens 530 can be attached with a helmet segment lift mechanism 550. This allows the welding operator to have access to the outside without having to remove the helmet. This can also be utilized to allow better, wider range visibility when chipping or grinding by having an optional clear plastic type lens 540 under the helmet segment with lens 530. There are a number of ways this function can be accomplished so it is not defined by the patent claims.

CONCLUSION, RAMIFICATION, AND SCOPE

This invention describes a welding helmet that encloses a welders head on five sides and covers a portion of their neck. This helmet apparatus improves a welding operators working environment. It provides clean air that reduces welding fume levels in their breathing zone below the maximum recommended levels. It does this while improving the working environment for one of the most objectionable welding environmental issues, excess heat. By providing cool air to the welders head and neck area their whole body will feel cooler. Studies have shown cooling the head area reduces sweating in other parts of the body.

The fact that a welders overall environment and working conditions are improved will provide incentive for them to use the helmet. The added advantage of having reduced burns from spatter in the head and neck area, especially when welding overhead, is another benefit of this fully enclosed welding helmet.

The discovery that using cooled air being exhausted from the helmet to cool the hot side heat sink of a thermoelectric module came about by chance when testing a device defined in patent application Ser. No. 12/455,667 filing date May 29, 2009 entitled Clean, Cool, Comfortable Welding Helmet.

Tests were made by delivering air into a closed container simulating a welding helmet with a tight fitting skirt. A commercial 45 watt thermoelectric cooling module incorporating aluminum hot side and cold side heat sinks was employed. A 60 mm diameter fan directed air from a duct arrangement into an opening in the top of the simulated helmet. Air entered the duct at one end and was channeled past the cool side heat sink. The 60 mm fan was located at the other end of the closed duct causing the air to enter the simulated helmet. A 55 mm hole was placed near the bottom of the sealed simulated helmet container so the volume air flow could be estimated by measuring flow velocity employing an impeller driven digital anemometer. The flow rate was determined to be approximately 200 liters/minute, more than sufficient to meet National Institute of Occupational Safety and Health requirements. Temperatures were measured digitally at locations before and after the cool heat sink.

When measuring air flow rates it was observed that the cool, clean air coming from the exit hole might be directed at the hot side aluminum heat sink to define if an improvement in system efficiency could be achieved. This is an unusual arrangement for a thermoelectric module since it appears to waste cooled air. However for this unique application the air flow must be high to meet breathable air requirements and therefore the exhaust air could be made available to perform a further function. A hose was attached to the 55 mm exit exhaust hole in the simulated helmet container. The exhaust air was directed over 8 of the 35 mm high aluminum fins on the hot side heat sink. The voltage and amperage powering the thermoelectric module were measured for all of the tests using a precision shunt and digital volt meters. It was approximately the same value for all tests ranging from 42 to 44 watts. For these tests the airflow configuration was not optimized for the most effective cooling of the hot heat sink. The results were very surprising and unexpected.

The following table shows the average measurements of several tests of each condition, with and without exhaust air cooling the heat sink. Repeat tests showed reproducible and essentially the same results.

| Cooling of Hot Heat Sink | Change in Temperature Measured Before and After Hot Side Cooling Heat Sink | | |
| --- | --- | --- | --- |
| | After 5 Minutes of Operation | After 10 Minutes of Operation | After 15 Minutes of Operation |
| Convection Cooling Only | −2.2 deg. C. | −1.7 deg. C. | −1.5 deg. C. |
| Enhanced with Cooled Helmet Exhaust Air | −3.9 deg. C. | −3.6 deg. C. | −3.6 deg. C. |

As seen in the temperature results in the above table, enhancing the cooling of the hot side heat sink increased the amount of air cooling and reduction in air temperature by over two fold. For some situations, this increase in efficiency of cooling provides an ability to use a portable energy source carried on the welder's body versus the optional external power source.

The suggested use of an external power source including that readily available from welding power provides the energy required for all welding situations without the need for a portable energy source that requires recharging. This allows a fan of sufficient capacity to draw air thorough a quality filter to capture potentially hazardous constituents of welding fumes. This externally supplied power allows the required cooling capacity thermoelectric cooling module(s) to be used to significantly lower the ambient air temperature to essentially any level desired. This allows the welding operator to have sufficient cooling to improve their overall work environment regardless of the ambient conditions. The relatively small energy consumed by this helmet is only a small fraction of the typical power used when welding and available from a welding power supply. Typical welding power used in arc welding ranges from 6000 to in excess of 10,000 watts compared to the approximately 50 to perhaps 100 watts needed to power the helmet. Therefore utilizing the welding power to supply energy for the helmet would not affect the weld performance or welding power supply capacity.

The above description contains many specificities to provide illustrations of some of the embodiments. However it is understood that other obvious items might be added such as various construction configurations for the external canister. Functions such as using electronic controls to set and or automatically limit the minimum achievable temperatures were also not delineated, although these are functionally easy to accomplish. Thus the scope of the invention should be determined by the appended claims and their legal equivalents, rather than the examples given.

I claim:

1. A hose supplied helmet apparatus that encloses the front, right side, left side, top and back of the head of a welding operator and comprises:
   a) an auto-darkening welding lens located in the front portion of said hose supplied helmet apparatus that when an electric arc is present changes from essentially transparent to a dark shade, and
   b) a skirt added to said hose supplied helmet apparatus wherein said skirt is made of a flexible, fire resistant material and attaches to the bottom of said hose supplied helmet apparatus to seal said skirt to said hose supplied helmet apparatus, and
   c) wherein said skirt may be attached to said hose supplied helmet apparatus such that it provides some portion of the enclosure of the back, sides and rear portion of the top of said hose supplied helmet apparatus, and
   d) a tie means located around said skirt to bring said skirt in close proximity to the neck of said welding operator, and
   e) said skirt may be of sufficient length to be placed under a shirt or jacket collar, and
   f) an external container is part of the hose supplied helmet apparatus to which a suitable belt or shoulder straps is affixed, allowing said welding operator to carry said external container on the body of the welding operator, and
   g) wherein one construction arrangement of said external container has two internal sections separated by an internal baffle of a predetermined thickness, an input air section and an exhaust air section, and
   h) an air filter is located at one end of said input air section of said external container to capture harmful particles of welding fume and prevent them from passing through said air filter, and
   i) an electric motor powered cooling fan is located in said input air section, and
   j) an electrically powered thermoelectric cooling module is sandwiched between a hot heat sink and a cold heat sink, and
   k) both said hot heat sink and said cold heat sink have a heat transfer surface consisting of fins or pins for providing a heat transfer surface, and
   l) said heat transfer surface of said cold heat sink is located in said input air section such that the air passing through said air filter communicates with said cold heat sink, and
   m) said air passing through said air filter transports cooled, clean air through a cooled air opening located at the opposite end of said input air section from the end having said air filter where said cooled air opening is approximately the same cross sectional area as an inlet cooled air hose of a predetermined cross section that is attached over said cooled air opening, and
   n) said inlet cooled air hose transports said cooled, clean air to the top front section of said hose supplied helmet apparatus and said inlet cooled air hose is attached over an inlet opening in said hose supplied helmet where said inlet opening is approximately the same cross sectional area as said inlet cooled air hose and the cooled, clean air passing through said inlet opening communicates with the head and face of said welding operator, and
   o) one end of an exhaust air hose of a predetermined size is attached over at an exhaust opening located in said hose supplied helmet apparatus where said exhaust opening is approximately the same cross sectional area as said exhaust air hose and said exhaust air hose transports a majority of the air that entered said hose supplied helmet apparatus from said inlet cooled air hose, and
   p) the opposite end of said exhaust air hose from the end attached to said hose supplied helmet is attached over an exhaust inlet opening located at one end of said exhaust air section of said external container where said exhaust inlet opening is approximately the same cross sectional area as said exhaust air hose, and
   q) said heat transfer surface of said hot heat sink is located in said exhaust air section, and
   r) the exhaust air entering said exhaust air section is directed so it is in communication with said hot heat sink before being expelled to the outside atmosphere through an opening located at the opposite end of said exhaust air passage from the end where said exhaust air hose is attached, and
   s) a power wire is attached to said external container and supplies electric power to said cooling fan and said thermoelectric cooling module from an outside source.

2. The hose supplied helmet apparatus of claim 1, wherein said power wire is replaced with a portable power source for supplying power and said portable power source is affixed to said external container or to an alternate means adaptable to be attached to the body of said welding operator.

3. The hose supplied helmet apparatus of claim 1, wherein said hose supplied helmet apparatus is powered by a DC power source having a voltage below about 24 volts obtained from a DC converter powered from an AC power source or a DC power source supplied by a welding power source employing an AC/DC to DC converter connected to said welding power source.

4. The hose supplied helmet apparatus of claim 1, including a control module and a temperature control knob such that a welding operator can adjust the desired temperature.

5. The hose supplied helmet apparatus of claim 4, wherein said power wire is replaced with a portable power source for supplying power and said portable power source is affixed to said external container or to an alternate means adaptable to be attached to the body of said welding operator.

6. The hose supplied helmet apparatus of claim 4, wherein said hose supplied helmet apparatus is powered by a DC power source having a voltage below about 24 volts obtained from a DC converter powered from an AC power source or a DC power source supplied by a welding power source employing an AC/DC to DC converter connected to said welding power source.

7. The hose supplied helmet apparatus of claim 1, including an electrically powered hot heat sink fan that is located in said exhaust air passage to increase air flow and further increase cooling of said hot heat sink.

8. The hose supplied helmet apparatus of claim 7, wherein said power wire is replaced with a portable power source for supplying power and said portable power source is affixed to said external container or to an alternate means adaptable to be attached to the body of said welding operator.

9. The hose supplied helmet apparatus of claim 7, wherein said hose supplied helmet apparatus is powered by a DC power source having a voltage below about 24 volts obtained from a DC converter powered from an AC power source or a DC power source supplied by a welding power source employing an AC/DC to DC converter connected to said welding power source.

10. The hose supplied helmet apparatus of claim 1, wherein said hose supplied helmet apparatus is constructed so as to also meet the requirements of a hard hat.

* * * * *